(12) United States Patent
Fisher et al.

(10) Patent No.: US 7,354,749 B2
(45) Date of Patent: Apr. 8, 2008

(54) DECELLULARISATION OF MATRICES

(75) Inventors: John Fisher, Leeds (GB); Catherine Booth, Leeds (GB); Eileen Ingham, Leeds (GB)

(73) Assignee: The University Leeds, Leeds (GB)

( * ) Notice: Subject to any disclaimer, the term of this patent is extended or adjusted under 35 U.S.C. 154(b) by 341 days.

(21) Appl. No.: 10/478,198

(22) PCT Filed: May 20, 2002

(86) PCT No.: PCT/GB02/02341

§ 371 (c)(1),
(2), (4) Date: Apr. 7, 2004

(87) PCT Pub. No.: WO02/096476

PCT Pub. Date: Dec. 5, 2002

(65) Prior Publication Data

US 2004/0157206 A1    Aug. 12, 2004

(30) Foreign Application Priority Data

May 24, 2001 (GB) ................................ 0112586.3

(51) Int. Cl.
*C12N 9/00* (2006.01)
*C12N 9/48* (2006.01)
(52) U.S. Cl. ..................... 435/183; 435/212; 424/94.2; 424/93.1
(58) Field of Classification Search ................ 435/183, 435/212; 424/94.2, 93.1
See application file for complete search history.

(56) References Cited

U.S. PATENT DOCUMENTS

| | | | |
|---|---|---|---|
| 4,323,358 A | | 4/1982 | Lentz et al. |
| 4,776,853 A | * | 10/1988 | Klement et al. ............. 8/94.11 |
| 6,100,064 A | | 8/2000 | Burke et al. |
| 6,147,080 A | | 11/2000 | Bemis et al. |
| 6,194,153 B1 | | 2/2001 | St. George-Hyslop et al. |
| 6,962,814 B2 | * | 11/2005 | Mitchell et al. ............ 435/402 |

FOREIGN PATENT DOCUMENTS

| | | |
|---|---|---|
| EP | 0 564 786 A2 | 10/1993 |
| WO | WO 99/41981 A1 | 8/1999 |
| WO | WO 02/14480 A2 | 2/2002 |

OTHER PUBLICATIONS

International Search Report, PCT/GB 02/02341.

* cited by examiner

*Primary Examiner*—Ruth A Davis
(74) *Attorney, Agent, or Firm*—Myers Bigel Sibley & Sajovec, PA

(57) ABSTRACT

A method of preparing matrices or tissue engineered biomaterials for implantation, and in particular to a method of improving decellularisation of matrices or tissue engineered biomaterials prior to implantation. The method employs a single anionic detergent in combination with protease inhibitors.

29 Claims, 2 Drawing Sheets

DECELLULARISATION OF MATRICES

RELATED APPLICATION

This application claims priority from PCT Application PCT/GB02/02341, filed 20 May 2002, which claims priority from British Application No. 0112586.3, filed 24 May 2001. These disclosures are hereby incorporated by reference herein in their entireties.

The present invention relates to a method of preparing matrices or tissue engineered biomaterials for implantation, and in particular to a method of improving decellularisation of matrices or tissue engineered biomaterials prior to implantation.

BACKGROUND TO THE INVENTION

A large variety of body implants are known for medical uses such as substitute vascular prostheses, skin dressings and coverings, and for other purposes. The implant material can be synthetic or body tissues from the same species or other species as the species to be implanted. When body tissues and structures are to be implanted, they may be used fresh from the donor but in many cases, it is preferred to have some means of preserving the implant tissue for later use. There are several preservation techniques currently available including cryopreservation and chemical fixation with cross-linking agents such as glutaraldehyde, polyglycidyl ether and carbodiimide. In order to prepare the implant tissue for later use it is desirable to decellularise the tissue prior to storage whilst minimising any damage to the physical structure of the tissue matrix itself. This decellularisation can be important in improving the biocompatability and reducing the immunological reaction in the tissue graft.

It is known from the prior art to use anionic detergents such as sodium dodecyl sulphate (SDS) for the extraction of cellular components. SDS extraction was first described in U.S. Pat. No. 4,323,358 as a method of preventing or delaying the calcification of glutaraldehyde-fixed Hancock heart valve bioprosthesis, the method is referred to as the "Hancock T6 treatment". In this method, fixed tissue is contacted with SDS so as to retard calcification. However, serious limitations of the method have been reported (Bodnar E et al, *Thorac. Cardiovasc. Surgeon.* 1985 34: 82-85; Courtman D W et al, *J Biomed Mater Res.* 1994 28: 655-666; Wilson G J et al. *ASAIO Trans* 1990 36: M340-343). These researchers all report that SDS has a deleterious effect on heart valve extracellular matrix (ECM) and in particular on the collagen and elastin fibre components.

In order to mitigate the effects of SDS on ECM, U.S. Pat. No. 4,776,853 describes the use of an earlier pre-treatment with other non-ionic detergents, such as Triton X-100 so that SDS is only employed as the second detergent in a multi-stage detergent decellularisation program.

A further problem associated with decellularising tissue implant is to minimise the degradation to the ECM during the process. It is known to use protease inhibitors to prevent such degradation during incubation with a non-ionic detergent in the first stage of the multistage detergent decellularisation program and also to use them to prevent naturally occurring proteases from attacking collagens. There are a number of different proteases that reside within the tissue matrix, either in direct association with the cells themselves or bound within the ECM. One of the largest of the protease families, the matrix metalloproteases (MMPs), has a wide range of substrate specificities including collagen, laminin, fibronectin and elastin. Another important family of matrix-degrading proteases are the plasminogen activators, which generates the broad specificity protease plasmin from the abundant zymogen plasminogen. As well as proteolytic activity, plasmin has the further ability of activating members of the MMP family. However, most of the protease inhibitors are inherently toxic which is undesirable if the matrix is to be seeded with living cells and implanted into a human or animal. Moreover, some of the protease inhibitors used so far, for example PMSF, are extremely unstable in solution having a half life of less than 1 hour, and since decellularisation is a lengthy process i.e. several days, this limits the choice of inhibitors that have sufficient half lives.

A method which could simplify the decellularisation process whilst minimising damage to ECM would offer significant advantage over current practices.

STATEMENT OF THE INVENTION

In its broadest aspect, the present invention provides a method of decellularising a tissue matrix using an anionic detergent at a concentration sufficient to effect decellularisation but at a concentration which maintains the histoarchitecture of the ECM, the sole anionic detergent being used in conjunction with protease inhibitors.

According to a first aspect of the invention there is provided a method of preparing biological material for implantation comprising the steps of:
(i) incubating the biological material with a buffer solution at a mild alkaline pH which includes active amounts of a proteolytic inhibitor;
(ii) incubating the biological material with an anionic detergent at a mild alkaline pH at a concentration which is sufficient to effect decellularisation but which maintains the histoarchitecture of the biological material;
(iii) washing the biological material with a buffer solution at a mild alkaline pH both with and without active amounts of proteolytic inhibitors;
(iv) incubating the biological material with one or more enzymes selected from the group comprising DNase Type I, DNase Type II, and/or Rnase and optionally;
(v) placing the biological material in a cryoprotectant medium.

Preferably the method does not include any additional detergent incubation steps.

Reference herein to decellularisation is intended to include the removal of cellular membranes, nucleic acids, lipids, cytoplasmic components and retaining an ECM having as major components collagens and elastins.

Preferably, the buffer solution is hypotonic or isotonic. It will be appreciated that each may be used either as the sole buffer or in combination at different stages of the method and that use of hypotonic or isotonic buffer is not intended to limit the scope of the present application.

The method may include the further step of cryopreserving the biological material in a cryogen such as liquid nitrogen until required.

Preferably, the proteolytic inhibitors are ethylene diamine tetraacetic acid (EDTA) and Aprotinin.

We have found Aprotinin particularly effective as a proteolytic inhibitor and of particular utility because of its low toxicity, stability in solution at different pHs and stability at a variety of different temperatures.

Typically, EDTA is used at a concentration range of 1 to 100 mM or 0.01-1.0% (w/v) and typically at 10 mM or 0.1% and Aprotinin at a concentration range of 1-100 KIU and typically at 10 KIU.

Preferably, the mild alkaline conditions of step (i) are in the range of pH above 7.0 and up to pH 10.0, and more preferably are at pH 8.0.

Preferably, the incubation period of step (i) of the method is for between 8 to 20 hours and more preferably is for 14 hours.

Preferably, the anionic detergent is sodium dodecyl sulphate (SDS) or sodium deoxycholate.

Preferably, SDS is used at a concentration equal to or below 0.1% (w/v), and equal to or above 0.03% (w/v).

Reference herein to the term % (w/v) refers to the percentage in weight (grams) per unit volume (100 ml), thus 0.1% w/v is equivalent to 0.1 gm dissolved in 100 ml.

Prior art methods in which SDS has been suggested for decellularisation use concentrations of SDS equal to or greater than 1% (w/v) in order to effect decelluarisation. We have found that using anionic detergents at this concentration results in destabilisation of protein interactions and/or solubilisation thus leading to degradation of ECM proteins. It has been the prevailing wisdom that SDS would not be effective below a concentration of 1% (w/v). However, our results have shown surprisingly, that a concentration of 0.1% or below it is effective for decellularisation when conducted in the presence of protease inhibitors and that there is no damage to the ECM.

Our further studies using a second non-ionic detergent such as Triton X-100, n-hexyl-$\beta$-D-glucopyranoside, TWEEN 20 and MEGA 10 and the zwitterionic detergent CHAPS showed no effect on the decellularisation produced by a low concentration of SDS alone. The results showed that use of a second detergent had no significant effect on decellularisation of porcine heart valves even after a period of 72 hrs. Thus, the present invention is of particular advantage in that we have shown that there is no requirement for a second non-ionic detergent. Accordingly, the present invention has obviated the need for a multistage detergent process.

Preferably, sodium deoxycholate is used at a concentration equal to or below 2.0% (w/v) and equal to or above 0.5% (w/v).

Preferably, the incubation period of step (ii) of the method is for between 20 to 28 hours and more preferably is for 24 hours.

Preferably, the mild alkaline conditions of step (ii) are in the range of pH above 7.0 and up to pH 10.0, and more preferably are at pH 8.0.

Preferably, the washing step (iii) of the method involves multiple washes, typically x3 washes with tris buffered saline (preferably 0.15M NaCl, 0.05M tris in distilled water) containing protease inhibitors (0.1% EDTA and 10 KIU/ml Aprotinin), and further, multiple washes, typically x3 washes with tris buffered saline without the protease inhibitors.

Preferably, the mild alkaline conditions of step (iii) are in the range of pH above 7.0 and up to pH 10.0, and more preferably are at pH 8.0.

Preferably, the incubation step (iv) of the method is for 4-6 hours at 37° C.

The DNase Type I, DNase Type II or Rnase are employed as low ionic strength solutions in an amount effective so as to eliminate nucleic acids and provide a tissue matrix of limited immunogenicity. Accordingly any other agents which are capable of the same function are included within the scope of the present invention.

Preferably, DNAse I is used at a concentration range of 5.0-100% µg/ml and typically at 20 µg/ml and RNAse A at a concentration range of 0.1-10 µg/ml and typically at 1 µg/ml.

Preferably, the biological tissue is prepared in step (v) of the method for storage by placement in a cryoprotectant, such as and without limitation, Dulbecco's modified eagles medium (DMEM) containing 10% (v/v) foetal bovine serum (FBS) and 10% (v/v) dimethyl sulphoxide (DMSO).

According to a further aspect of the invention there is provided a tissue implant comprising ECM from which have been removed cellular membranes, nucleic acids and other cytoplasmic components the tissue implant having been produced by the method of the present invention.

In summary, preferred embodiments of the present invention provides a method of decellularisation of a tissue matrix which results in no significant deleterious effects to the ECM proteins and subsequent histoarchitecture of the aortic valve, as assessed by both histological and biomechanical techniques and wherein a single anionic detergent such as SDS or sodium deoxycholate is used at a concentration sufficient to cause decellularisation;

as a single stage detergent;
at low concentrations that effect decellularisation whilst maintaining the ECM in good condition;
in combination with the protease inhibitors EDTA (as an inhibitor of MMPs) and Aprotinin (inhibitor of serine family of plasminogen activators);
for a period of about 24 hours;

According to a yet further aspect of the invention there is provided a product comprising a combination of an anionic detergent at a concentration hereinbefore described and a proteolytic inhibitor as hereinbefore described and optionally including a set of instructions for use thereof for use in the method of the present invention.

BRIEF DESCRIPTION OF THE DRAWINGS

Alternatively the product comprising may comprise concentrates for dilution and use in a method.

The present invention will now be described by way of example only with reference to the following Figures wherein.

DETAILED DESCRIPTION OF THE INVENTION

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs.

All publications, U.S. patent applications, U.S. patents and other references cited herein are incorporated by reference in their entireties.

Figures 1A, 1B:
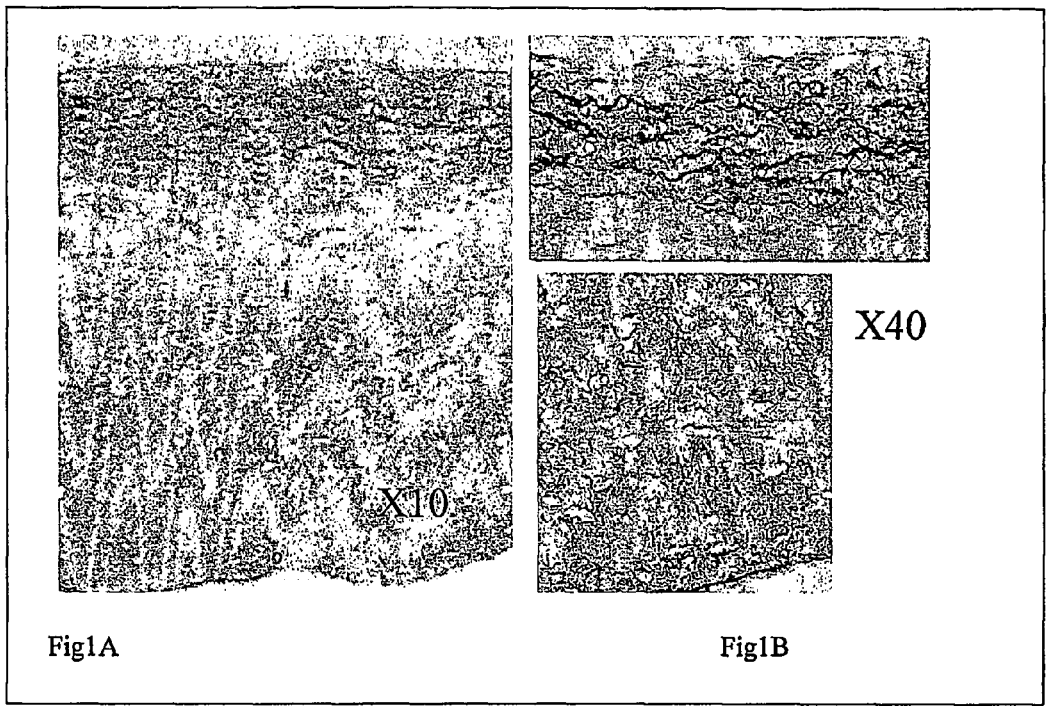
FIG. 1A illustrates a cross section of heart valve leaflet treated with 0.05% SDS solution at x10 magnification.
FIG. 1B illustrates FIG. 1A at x40 magnification.
Figures 2A, 2B:
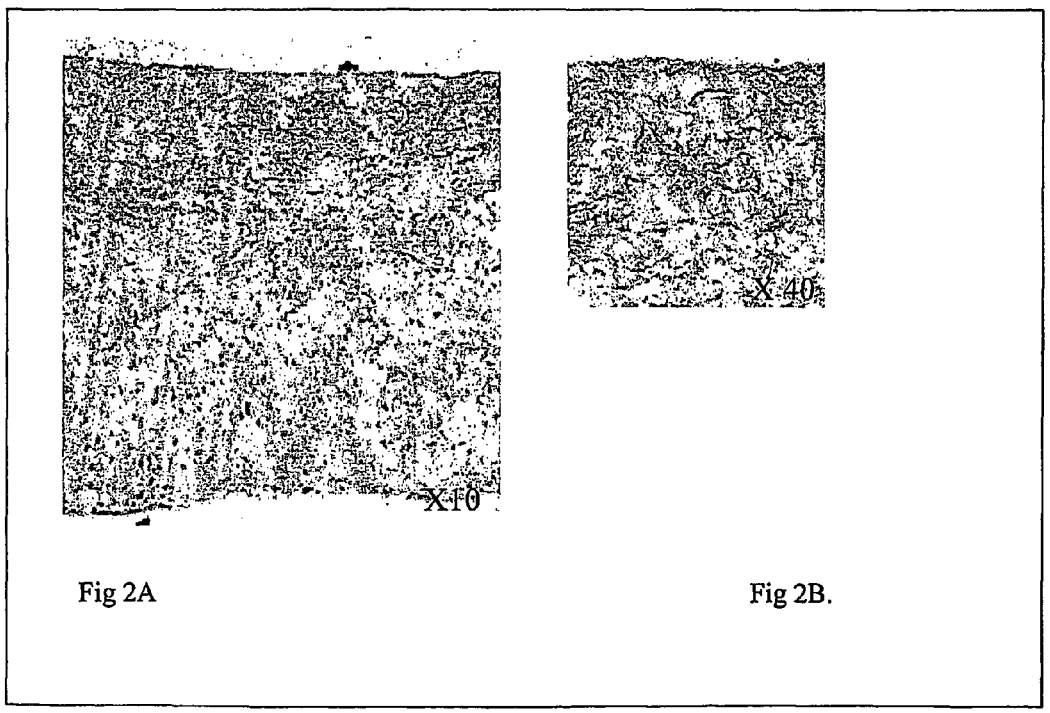
FIG. 2A illustrates a cross section of heart valve leaflet treated with 0.02% SDS solution at x10 magnification.
FIG. 2B illustrates FIG. 2A at x40 magnification.

With reference to FIGS. 1A and 1B there is shown a cross section of a heart valve leaflet treated with concentrations of 0.03% SDS. Total leaflet decellularisation was observed at this concentration. However, at concentrations below 0.05% (FIGS. 2A and 2B), whole cells or cell fragments were found to have been retained by the matrix. Cross section of a heart valve leaflet treated with 0.02% SDS is therefore a concentration below which decellularisation does not occur. It can be seen that cell fragments and whole cells have been retained within the matrix (Blue/black pigment). Following the method of the present invention, patella tendons may also be successfully decellularised (FIG. 3B).

EXAMPLE 1

Porcine Aortic Valves

Porcine hearts were procured from a local abattoir within 2 hours of slaughter and transported on ice to the laboratory. On arrival at the laboratory, aortic valve roots were dissected from the heart and washed in transport solution [Hanks' balanced salt solution (HBSS), 10 KIU/ml Aprotinin, 10 u/ml penicillin, 100 µg/ml streptomycin, 100 U/ml Nystatin, 10 mM HEPES pH7.6). The aortic valves were incubated overnight (14 hours) in hypotonic tris buffer (10 mM tris pH8, 0.1% (w/v) ethylene diamine tetraacetic acid (tDTA), 10 KIU Aprotinin in distilled water DW).

Subsequently, the aortic valves were incubated for 24 hours with shaking at ambient temperature in (0.05%-0.1%) (w/v) sodium dodecyl sulphate (SDS) or 0.5% sodium deoxycholate in hypotonic tris buffer. They were then washed (×3) with tris buffered saline (0.15M NaCl, 0.05M tris pH 7.6 in DW) containing protease inhibitors (0.1% w/v EDTA and 10 KIU/ml Aprotinin). They were then subjected to a further wash (×3) with tris buffered saline (TBS) without protease inhibitors.

The aortic valves were then incubated for 4-6 hours at 37° C. with DNAse I (20 µg/ml) and RNAse A (1 µg/ml). After this they were washed (×3) in TBS containing protease inhibitors. Finally, in preparation for storage they were placed in cryoprotectant [Dulbecco modified eagles medium (DMEM) containing 10% (v/v) foetal bovine serum (FBS) and 10% (v/v) dimethyl sulphoxide (DMSO) and cryopreserved in liquid nitrogen until they were required for implantation.

EXAMPLE 2

Porcine Patella Tendons

Porcine patella tendons were dissected and then washed in PBS. The tendons were incubated overnight (24 hours) in hypotonic Tris buffer (10 mM Tris pH 8, 0.1% ethylene diamine tetraacetate (EDTA), 10 KIU Aprotinin in distilled water (DW)]. Tendons were subsequently incubated for a further 24 hours with shaking at ambient temperature in 0.03-0.1% w/v sodium dodecyl sulphate (SDS) or 0.5% sodium deoxycholate in hypotonic Tris buffer. They were then washed (×3) with PBS containing protease inhibitors (0.1% EDTA and 10 KIU/ml Aprotinin).

Figure 3A:
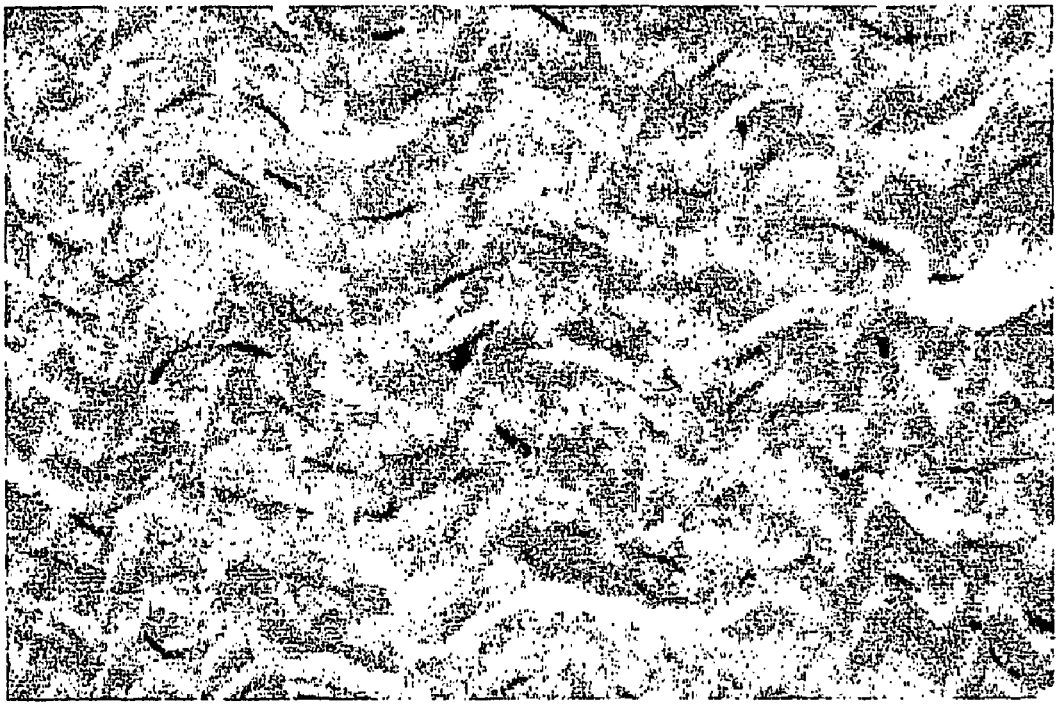
FIG. 3A illustrates a photomicrograph at x400 magnification of fresh porcine patellar tendon stained with heamatoxylin and eosin.
Figure 3B:
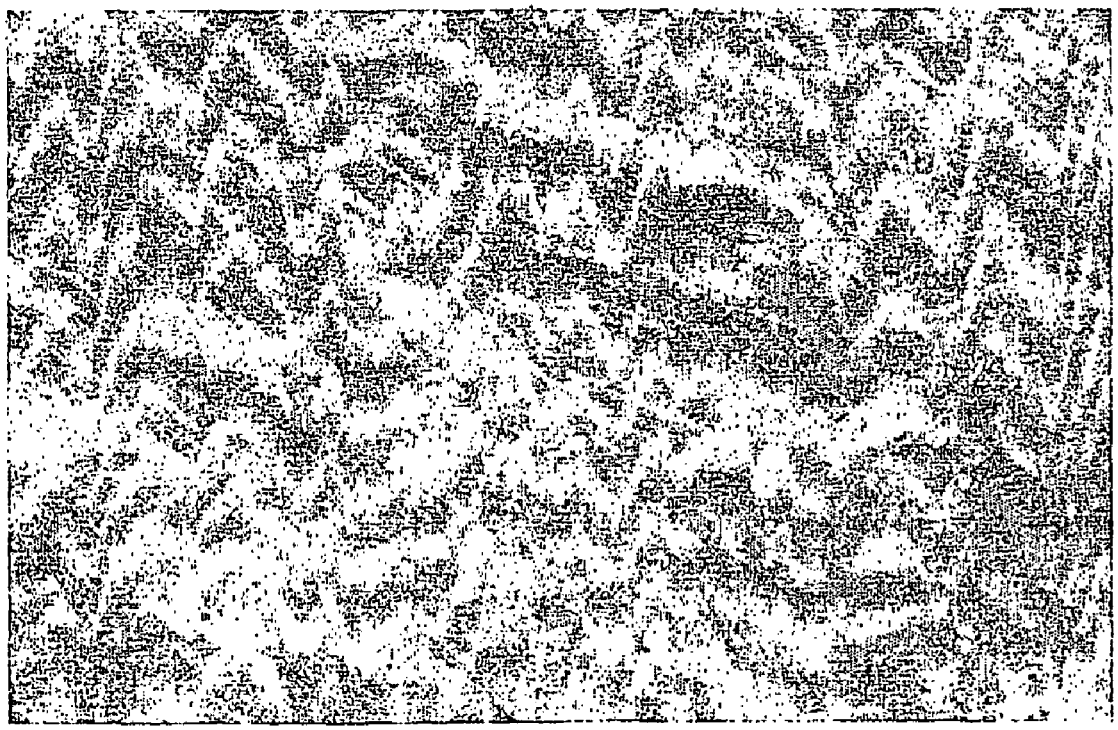
FIG. 3B illustrates a photomicrograph at x400 magnification of porcine patellar tendon following the de-cellularisation treatment according to the present invention.

With reference to FIG. 3A there is shown a photomicrograph of fresh porcine patella tendon, stained with heamatoxylin and eosin (×400). FIG. 3B shows a photomicrograph of porcine patellar tendon following de-cellularisation treatment as described above and also stained with heamatoxylin and eosin (×400). It is apparent from comparing the Figures that decellularisation has been achieved whilst maintaining the histoarchitecture of the material.

The invention claimed is:

1. A method of preparing donor biological material for implantation consisting essentially of:
   (i) incubating the donor biological material with a buffer solution at a mild alkaline pH, wherein the buffer solution comprises a proteolytic inhibitor;
   (ii) incubating the donor biological material with an anionic detergent at a mild alkaline pH at a concentration which is sufficient to effect decellularization but which maintains the histoarchitecture of the donor biological material, wherein said incubation is the sole incubation step with the detergent in said method of preparing the donor biological material for implantation and said anionic detergent is the sole detergent agent in the method;
   (iii) washing the donor biological material with a buffer solution at a mild alkaline pH, wherein the buffer solution comprises a proteolytic inhibitor;
   (iv) washing the donor biological material with a buffer solution at a mild alkali pH in the absence of a proteolytic inhibitor;
   (v) incubating the donor biological material with one or more enzymes selected from the group consisting of DNase Type I, DNase Type II, and/or RNase; and optionally
   (vi) placing the donor biological material in a cryoprotectant medium.

2. The method according to claim 1, wherein the buffer is hypotonic or isotonic.

3. The method according to claim 1, further comprising cryopreserving the donor biological material in a cryogen.

4. The method according to claim 3, wherein the cryogen is liquid nitrogen.

5. The method according to claim 1, wherein the proteolytic inhibitor is ethylene diamine tetraacetic acid (EDTA), Aprotinin or a combination thereof.

6. The method according to claim 5, wherein the EDTA is used at a concentration in the region of 1 to 100 mM or 0.01-1.0% (w/v).

7. The method according to claim 5, wherein EDTA is used at a concentration of 10 mM or 0.1% (w/v).

8. The method according to claim 5, wherein Aprotinin is used at a concentration range of 1-100 KIU.

9. The method according to claim 5, wherein Aprotinin is used at 10 KIU.

10. The method according to claim 1, wherein the mild alkaline conditions (i) are in the pH range of above 7.0 and up to pH 10.0.

11. The method according to claim 10, wherein the pH is 8.0.

12. The method according to claim 1, wherein the incubation period of (i) is from 8 to 20 hours.

13. The method according to claim 12, wherein the incubation period is 14 hours.

14. The method according to claim 1, wherein the anionic detergent is sodium dodecyl sulphate (SDS) or sodium deoxycholate.

15. The method according to claim 14, wherein SDS is used at a concentration in a range from 0.03% (w/v) to 0.1% (w/v).

16. The method according to claim 14, wherein sodium deoxycholate is used at a concentration in a range from 0.5% (w/v) to 2.0% (w/v).

17. The method according to claim 1, wherein the incubation period of (ii) is from 20 to 28 hours.

18. The method according to claim 17, wherein the incubation period is 24 hours.

19. The method according to claim 1, wherein the alkaline conditions of (ii) are in the pH range of above 7.0 to pH 10.0.

20. The method according to claim 19, wherein the pH is 8.0.

21. The method according to claim 1, wherein the washing of (iii) comprises multiple washes with iris buffered saline containing protease inhibitors and/or multiple washes with iris buffered saline without the protease inhibitors.

22. The method according to claim 21, wherein the buffer is 0.15 M NaCl, 0.05 M tris in distilled water with or without EDTA and Aprotinin.

23. The method according to claim 1, wherein the alkaline conditions of (iii) are in the pH range of above 7.0 to pH 10.0.

24. The method according to claim 23, wherein the pH is 8.0.

25. The method according to claim 1, wherein the incubation of (iv) is for 4-6 hours at 37° C.

26. The method according to claim 1, wherein DNase I is used at a concentration in the range of 5-100 µg/ml and RNase is used at a concentration in the range of 0.1-10 µg/ml.

27. The method according to claim 1, wherein the donor biological material is prepared in (vi) for storage by placement in a cryoprotectant comprising Dulbecco's modified eagles medium (DMEM) containing between 10-20% (v/v) fetal bovine selum (FBS) and 5-15% (v/v) dimethyl sulphoxide (DMSO).

28. A method of decellularizing a donor tissue matrix using an anionic detergent at a concentration sufficient to effect decellularization, but at a concentration which maintains a histoarchitecture of a heart valve extracellular matrix, the sole anionic detergent being used in conjunction with EDTA and Aprotinin protease inhibitors.

29. A method of preparing donor biological material for implantation consisting essentially of:
(i) incubating the donor biological material with a buffer solution at a mild alkaline pH, wherein the buffer solution comprises a proteolytic inhibitor selected from the group consisting of ethylene diamine tetraacetic acid (EDTA), Aprotinin and a combination thereof;
(ii) incubating the donor biological material with an anionic detergent at a mild alkaline pH at a concentration which is sufficient to effect decellularization but which maintains the histoarchitecture of the donor biological material, wherein said incubation is the sole incubation step with the detergent in said method of preparing the donor biological material for implantation;
(iii) washing the donor biological material with a buffer solution at a mild alkaline pH wherein the buffer solution comprises a proteolytic inhibitor selected from the group consisting of ethylene diamine tetraacetic acid (EDTA), Aprotinin and a combination thereof;
(iv) washing the donor biological material with a buffer solution at a mild alkali pH in the absence of a proteolytic inhibitor;
(v) incubating the donor biological material with one or more enzymes selected from the group consisting of DNase Type I, DNase Type II, and/or RNase; and
(vi) cryopreserving the donor biological material.

* * * * *

UNITED STATES PATENT AND TRADEMARK OFFICE
CERTIFICATE OF CORRECTION

PATENT NO. : 7,354,749 B2  
APPLICATION NO. : 10/478198  
DATED : April 8, 2008  
INVENTOR(S) : Fisher et al.

Page 1 of 1

It is certified that error appears in the above-identified patent and that said Letters Patent is hereby corrected as shown below:

Column 7, Claim 21, Lines 21 and 23: Please correct "iris buffered"
To read -- tris buffered --

Column 8, Claim 27, Line 3: Please correct "bovine selum"
To read -- bovine serum --

Signed and Sealed this

First Day of July, 2008

JON W. DUDAS  
*Director of the United States Patent and Trademark Office*